United States Patent [19]

Milam et al.

[11] Patent Number: 4,835,327

[45] Date of Patent: May 30, 1989

[54] METHOD FOR PRODUCING 1,2,4-TRICHLOROBENZENE

[75] Inventors: Joseph E. Milam, New Martinsville, W. Va.; William E. Wimer, Uniontown, Ohio

[73] Assignee: PPG Industries, Inc., Pittsburgh, Pa.

[21] Appl. No.: 938,495

[22] Filed: Dec. 5, 1986

[51] Int. Cl.$^4$ ............................................. C07C 17/12
[52] U.S. Cl. ................................. 570/208; 570/206; 570/207
[58] Field of Search ..................... 570/206, 208, 207

[56] References Cited

U.S. PATENT DOCUMENTS

| | | | |
|---|---|---|---|
| 3,130,007 | 4/1964 | Breck | 23/113 |
| 3,216,789 | 11/1965 | Breck et al. | 23/113 |
| 4,548,914 | 10/1985 | Chu | 502/85 |
| 4,570,023 | 2/1986 | Petruck et al. | 568/208 |
| 4,605,801 | 8/1986 | Julh et al. | 570/253 |
| 4,724,269 | 2/1988 | Suzuki et al. | 570/208 |
| 4,777,305 | 10/1988 | Cobb et al. | 570/208 |

FOREIGN PATENT DOCUMENTS

| | | | |
|---|---|---|---|
| 0112722 | 7/1984 | European Pat. Off. | 570/208 |
| 0118851 | 9/1984 | European Pat. Off. | 570/208 |
| 0154236 | 9/1985 | European Pat. Off. | 570/206 |
| 0171265 | 2/1986 | European Pat. Off. | 570/208 |
| 0092227 | 7/1981 | Japan | 570/207 |
| 57-77631 | 5/1982 | Japan | 570/206 |

OTHER PUBLICATIONS

H. F. Wiegandt et al., *Industrial and Engineering Chemistry*, vol. 43, No. 9, pp. 2167-2172 (1951).
Kirk-Othmer, *Encyclopedia of Chemical Technology*, 2d Ed., vol. 18, pp. 157-158 (1969).
L. Wilkosz, *Przemys Chemiczny*, vol. 51, No. 8, pp. 524-527 (1972).
D. W. Breck, *Zeolite Molecular Sieves*, pp. 156, 177, 361, 369 (1974).
Kirk-Othmer, *Encyclopedia of Chemical Technology*, 3d Ed., vol. 5, pp. 797-808, 819-827 (1979).
T. Huizinga et al., *Tetrahedron Letters*, vol. 21, pp. 3809-3812 (1980).
M. Windholz, *The Merck Index*, 10th Ed., p. 1454 (1983).

*Primary Examiner*—Werren B. Lone
*Attorney, Agent, or Firm*—George D. Morris

[57] ABSTRACT

1,2,4-Trichlorobenzene is produced by chlorinating benzene, chlorobenzene, meta-dichlorobenzene, ortho-dichlorobenzene, or a mixture of two or more thereof in a reaction medium comprising a liquid phase and a catalytic amount of zeolite L, zeolite Y, or a mixture thereof.

23 Claims, No Drawings

METHOD FOR PRODUCING 1,2,4-TRICHLOROBENZENE

BACKGROUND OF THE INVENTION 1,2,4-Trichlorobenzene is frequently produced by chlorinating benzene, chlorobenzene and/or ortho-dichlorobenzene and, less frequently, by chlorinating meta-dichlorobenzene. The formation of 1,2,4-trichlorobenzene is accompanied by the formation of various by-products such as 1,2,3-trichlorobenzene, more highly chlorinated materials including 1,2,4,5-tetrachlorobenzene and 1,2,3,4-tetrachlorobenzene, and sometimes degradation products. The coproduced by-products are undesirable in that they represent losses of one or more reactants to less beneficial materials than the desired 1,2,4-trichlorobenzene. In order to improve the production of 1,2,4-trichlorobenzene, the chlorination is usually conducted in the presence of a catalyst such as ferric chloride, with or without a promoter such as, for example, carbon disulfide, sulfur chloride, or elemental sulfur. R-values, hereinafter more fully defined, on the order of about 1.5 when the x-value, also hereinafter more fully defined, is about 3, are typical of such catalyzed reactions. The quantities of by-products, however, are still undesirably high.

THE INVENTION

It has now been discovered that 1,2,4-trichlorobenzene can be produced at high R-values by conducting the chlorination in the presence of particular forms of zeolite such that the x-value of the organic reaction mixture is in an appropriate range. Accordingly, the invention is the method comprising reacting benzene, chlorobenzene, meta-dichlorobenzene, ortho-dichlorobenzene, or a mixture of two or more thereof with chlorinating agent in a reaction medium comprising a liquid phase and a catalytic amount of zeolite L, zeolite Y, or a mixture thereof, to produce an organic reaction product comprising 1,2,4-trichlorobenzene wherein the x-value of the organic reaction product is in the range of from about 2.1 to about 3.2.

The reaction may broadly be characterized as a liquid phase reaction although some or all of the chlorination may be occurring within the pores of the zeolite catalyst.

The organic reaction product is removed from the reactor in which it was produced. Preferably it is removed as a liquid, but it may be vaporized and removed as a vapor. Alternatively, some of the organic reaction product may be removed as a liquid and some as a vapor.

A convenient scale of reference for monitoring chlorinations of this type is the "x-value" which reflects the degree of chlorination of the benzene-based compounds in the organic feedstock, in the liquid phase as the reaction progresses, and in the organic reaction product. The x-value is the value of x in the empirical formula for a mixture of such compounds: $C_6H_{6-x}Cl_x$. It may be calculated as follows:

$$x\text{-value} = \frac{B + 2C + 3D + 4E + 5F + 6G}{A + B + C + D + E + F + G}$$

where
A = moles of benzene present;
B = moles of monochlorobenzene present;
C = moles of dichlorobenzene (all isomers) present;
D = moles of trichlorobenzene (all isomers) present;
E = moles of tetrachlorobenzene (all isomers) present;
F = moles of pentachlorobenzene present; and
G = moles of hexachlorobenzene present.

The x-value of the organic reaction product is in the range of from 2.1 to about 3.2. In many cases the x-value of the organic reaction product is in the range of from about 2.3 to about 3.1. Preferably the x-value of the organic reaction product is in the range of from about 2.4 to about 3.0.

As used herein and in the claims, "R-value" is the ratio obtained by dividing the number of moles of 1,2,4-trichlorobenzene in the organic reaction product by the sum of the moles of 1,2,3-trichlorobenzene and higher chlorinated benzenes (viz., the tetrachlorobenzenes, pentachlorobenzene, and hexachlorobenzene) also in the organic reaction product. The R-value is a measure of the efficiency with which the benzene and/or chlorine-substituted benzene is chlorinated to produce 1,2,4-trichlorobenzene as contrasted with the production of the by-products 1,2,3-trichlorobenzene and higher chlorinated benzenes.

Although is not desired to be bound by any theory, it is believed that the tetrachloro and higher chlorinated benzenes result from the progressive chlorination of the trichlorobenzenes. For a given organic feedstock and a given set of reaction conditions, as chlorination progresses the proportion of 1,2,4-trichlorobenzene in the liquid phase (and hence the R-value) increases to a maximum and then declines as the proportions of higher chlorinated benzenes increase. Inasmuch as 1,2,4-trichlorobenzene is the principally desired product, high R-values are ordinarily desired. In most cases, the R-value of the organic reaction product is at least about 2.5. Often the R-value is at least about 3. In many cases the R-value is at least about 4. Preferably, the R-value is at least about 5. Still higher R-values may often be obtained. The R-value of the organic reaction product is frequently at least about 6 or even at least about 7. In some instances organic reaction products having very high R-values are obtained, such as those wherein the R-value is at least about 9 or even at least about 11.

Zeolite L and zeolite Y are both known crystalline zeolites and are described in detail in U.S. Pat. No. 3,216,789 and U.S. Pat. No. 3,130,007, respectively. The disclosures of both of these U.S. patents are, in their entireties, incorporated herein by reference. Both zeolite L and zeolite Y contain exchangeable cations. The cations in any particular crystal of zeolite L or zeolite Y may be essentially the same or they may be different and in varying proportions. In general, the exchangeable cations are metal cations or cations, as for example, hydrogen and ammonium, which behave like metal cations in that they may be replaced for other exchangeable cations without causing a substantial alteration of the basic crystal structure of the zeolite. Most often the exchangeable metal cations are monovalent, divalent, or trivalent, particularly those of Groups I, II and III of the Periodic Table. Cations of many of the transition metals, lanthanides, and actinides may be used when desired. In the present invention, the exchangeable cations most commonly employed in the zeolite L and zeolite Y are sodium, potassium, calcium and/or hydrogen, although other cations may be used when desired. Potassium zeolite L and sodium zeolite Y, in which most of the exchangeable cations are potassium cations and sodium cations, respectively, are preferred for use in the present invention.

The organic feedstock for the reaction comprises benzene, chlorobenzene, meta-dichlorobenzene, ortho-dichlorobenzene, or a mixture of two or more thereof. Other compounds may also be present. In most cases the feedstock comprises at least about 10 percent by weight benzene, chlorobenzene, meta-dichlorobenzene, ortho-dichlorobenzene or a mixture of two or more thereof. Frequently the organic feedstock comprises at least about 50 percent by weight benzene, chlorobenzene, meta-dichlorobenzene, ortho-dichlorobenzene, or a mixture of two or more thereof. At least about 90 percent by weight of one or more of these compounds is preferred.

The most favored feedstocks are those comprising at least about 30 percent by weight meta-dichlorobenzene, ortho-dichlorobenzene or a mixture thereof. Often the feedstock comprises at least about 60 percent by weight meta-dichlorobenzene, ortho-dichlorobenzene, or a mixture thereof. Preferably the feedstock comprises at least about 90 percent by weight of either or both of these compounds.

The reaction may be conducted batchwise, continuously, semi-batchwise, or semi-continuously. Continuous reactions in which chlorinating agent and feedstock are continuously introduced to a reactor containing the appropriate zeolite and in which liquid reaction product is continuously removed from the reactor, are preferred. Semi-batchwise reactions, especially those in which chlorinating agent is added continuously or intermittently to a batch of the feedstock, are often employed. Semi-continuous reactions in which one of the reactants is added continuously to a reactor containing the appropriate zeolite while the other reactant is added intermittently, may be used. Strictly batchwise reactions are usually employed only when the chlorinating agent either produces molecular chlorine slowly or reacts slowly with benzene, chlorobenzene, ortho-dichlorobenzene, meta-dichlorobenzene or a mixture of two or more thereof, under the conditions of the reaction. The reaction may be conducted in the presence of extrinsic diluent or no extrinsic diluent may be used. In the semi-batchwise reaction method, the weight ratio of zeolite L, zeolite Y, or a mixture thereof to the benzene, chlorobenzene, ortho-dichlorobenzene, meta-dichlorobenzene, or a mixture of two or more thereof, initially present may vary widely. In most cases, however, the weight ratio is in the range of from about 0.1:100 to about 20:100. Often the weight ratio is in the range from about 1:100 to about 15:100. A weight ratio in the range of from about 2:100 to about 10:100 is preferred.

Irrespective of the type of reaction, the chlorinating agent may be any material which will chlorinate, either directly or indirectly, benzene, chlorobenzene, ortho-dichlorobenzene, meta-dichlorobenzene, or a mixture of two or more thereof. Examples of chlorinating agents include molecular chlorine, sulfuryl chloride, sulfur monochloride, N-chlorosuccinimide, phosphorous pentachloride, and chlorine monoxide. The preferred chlorinating agent is molecular chlorine.

In many cases only a portion of the chlorine content of the chlorinating agent is available for the desired chlorination. This may be due to a variety of causes. Undesired side reactions, for example, may sometimes consume a portion of the chlorine. Often, the nature of the reaction itself is such that, even ideally, only a portion of the chlorine content of the chlorinating agent is available for chlorination. As an example of the latter situation, the reaction of one mole of elemental molecular chlorine with ortho-dichlorobenzene results in the evolution of one mole of hydrogen chloride. The evolved hydrogen chloride is often recovered and used to produce other useful materials. It may be seen that the availability of chlorine atoms for desired chlorination is a factor to be considered in choosing relative proportions of the chlorinating agent and the feedstock to be used in conducting the reaction. Other factors to be considered include the x-value of the feedstock and the x-value to be achieved in the organic reaction product. In general, sufficient chlorinating agent should be introduced to the reaction to accomplish the desired degree of chlorination of the feedstock.

The temperatures at which the reaction is conducted are similarly subject to wide variation but ordinarily they are in the range of from about 40° C. to about 200° C. In many cases the temperatures are in the range of from about 70° C. to about 130° C. From about 90° C. to about 110° C. is preferred.

The pressures at which the reaction is conducted may also be varied widely. Ambient atmospheric pressure or slightly higher is generally employed although greater or lesser pressures may be used. In most cases the pressure is in the range of from about 0 to 700 kilopascals, gauge. Frequently, the pressure is in the range of from about 0 to about 350 kilopascals, gauge.

The 1,2,4-trichlorobenzene may be recovered from the organic reaction product by any of the various techniques known to the art. Distillation and/or crystallization are examples of techniques that may be employed. When desired, the benzene, monochlorobenzene, meta-dichlorobenzene and/or ortho-dichlorobenzene values may also be recovered from the organic reaction product and recycled to the chlorination reactor as all or a portion of new feedstock.

1,2,4-Trichlorobenzene has a number of uses including for example, as an intermediate in the manufacture of the herbicide 3,6-dichloro-o-anisic acid, as the starting material in the manufacture of 2,5-dichlorophenol, as a high-boiling solvent for oil-soluble dyes, as a degreasing solvent, as a dielectric fluid, as a lubricating-oil additive, and as a termite exterminant.

The invention is further described in conjunction with the following examples which are to be considered illustrative rather than limiting, and in which all parts are parts by weight and all percentages are percentages by weight unless otherwise specified. Abbreviations employed include the following: DCB=dichlorobenzene, TCB=trichlorobenzene, Tetra=tetrachlorobenzene, Penta=pentachlorobenzene, BCB=bromochlorobenzene. Inasmuch as bromochlorobenzene is not within the formula $C_6H_{6-x}Cl_x$, any amount of this material present was ignored in calculating x-values and R-values.

EXAMPLE I

Activated rare earth-form zeolite Y catalyst was prepared by heating 25.31 grams of rare earth-form zeolite Y extrudate (Linde SK 500 1.5875 millimeter extrudate) in an oven at 400° C. overnight.

A 250 milliliter, 2-neck round bottom flask equipped with a stirrer, a side arm, a thermometer, a water cooled reflux condenser, a dip tube having a capillary bore, and a hot water bath, was charged with 147.01 grams of ortho-dichlorobenzene of 98.70 percent purity and 6.25 grams of the activated rare earth-form zeolite Y catalyst. The apparatus was shielded from light using aluminum foil and black vinyl tape. The charged materials were heated to 50° C. and molecular chlorine was introduced below the surface of the liquid via the dip tube at a rate of 0.30 gram per minute for 4 hours while the temperature was maintained at 50° C. Each hour after the beginning of chlorine introduction, a sample was taken. The sample was then analyzed and the x-value and the R-value were calculated. The results are shown in Table 1.

TABLE 1

| Time, hours | 0 | 1 | 2 | 3 | 4 |
|---|---|---|---|---|---|
| Product Distribution, wt. percent | | | | | |
| Meta-DCB | 0.02 | 0 | 0 | 0 | 0 |
| Para-DCB | 1.19 | 1.05 | 0.94 | 0.79 | 0.65 |
| Ortho-DCB | 98.70 | 69.38 | 48.94 | 28.19 | 11.47 |
| 1,4-BCB | 0.02 | 0.02 | 0.01 | 0 | 0 |
| 1,2,4-TCB | 0.06 | 23.19 | 39.05 | 54.78 | 64.75 |
| 1,2,3-TCB | 0 | 5.94 | 9.71 | 12.77 | 13.89 |
| Tetras | 0 | 0.39 | 1.36 | 3.47 | 8.85 |
| x-value | 2.00 | 2.26 | 2.46 | 2.69 | 2.93 |
| R-value | | 3.70 | 3.60 | 3.49 | 3.04 |

EXAMPLE II

Activated potassium-form zeolite L catalyst was prepared by heating 22.23 grams of potassium-form zeolite L powder (Linde ELZ-L) in an oven at 400° C. overnight.

The apparatus of Example I was modified by replacing the hot water bath with an electric heating mantle connected to a temperature controller. The flask was charged with 228.55 grams of ortho-dichlorobenzene of 98.65 percent purity and 15.5 grams of the activated potassium-form zeolite L catalyst. The charged materials were heated to 110° C. and molecular chlorine was introduced below the surface of the liquid via the dip tube at a rate of 0.46 gram per minute for 4 hours. During approximately the first 45 minutes the temperature was somewhat erratic due to difficulties with the temperature controller. The temperature was held at 110° C. thereafter. Each hour after the beginning of chlorine introduction, a sample was taken. The sample was then analyzed and the x-value and R-value were calculated. The results are shown in Table 2.

TABLE 2

| Time, hours | 0 | 1 | 2 | 3 | 4 |
|---|---|---|---|---|---|
| Product Distribution, wt. percent | | | | | |
| Meta-DCB | 0.02 | 0.01 | 0.01 | 0 | 0 |
| Para-DCB | 1.22 | 1.12 | 1.08 | 1.02 | 0.99 |
| Ortho-DCB | 98.65 | 82.01 | 65.91 | 52.06 | 40.51 |
| 1,4-BCB | 0.03 | 0.02 | 0.02 | 0.02 | 0.01 |
| 1,2,4-TCB | 0.08 | 15.10 | 29.40 | 41.60 | 51.19 |
| 1,2,3-TCB | 0 | 1.62 | 3.17 | 4.52 | 5.75 |
| 1,2,4,5-Tetra | 0 | 0.04 | 0.16 | 0.32 | 0.61 |
| 1,2,3,4-Tetra | 0 | 0.08 | 0.26 | 0.48 | 0.83 |
| x-value | 2.00 | 2.14 | 2.29 | 2.42 | 2.54 |
| R-value | | 8.77 | 8.35 | 8.01 | 7.35 |

EXAMPLE III

Activated potassium-form zeolite L catalyst was prepared by heating potassium-form zeolite L powder (Toyo Soda) in an oven at 200° C. overnight.

A 500 milliliter, 4-neck round bottom flask painted black to exclude light was equipped with a mechanical stirrer, a thermometer, a water cooled reflux condenser connected to an aqueous sodium hydroxide scrubber, a rubber septum through which samples were withdrawn, and a hot water bath. The shaft of the stirrer had a hollow bore and an outlet orifice near the paddle. The flask was charged with 147.0 grams of meta-dichlorobenzene and 5.00 grams of the activated potassium-form zeolite L catalyst. The charged materials were heated and molecular chlorine was introduced below the surface of the liquid via the hollow bore and outlet orifice at a rate of 0.30 gram per minute for 4 hours. Each hour after the beginning of a chlorine introduction, a sample was taken. The sample was then analyzed and the x-value and R-value were calculated. The temperatures and results are shown in Table 3.

TABLE 3

| Time, hours | 0 | 1 | 2 | 3 | 4 |
|---|---|---|---|---|---|
| Temperature, °C. | 91 | 95.5 | 96 | 96 | 96 |
| Product Distribution, moles | | | | | |
| Meta-DCB | 1.0000 | 0.8899 | 0.7770 | 0.6641 | 0.5734 |
| 1,2,4-TCB | 0 | 0.1018 | 0.2059 | 0.3109 | 0.3931 |
| 1,2,3-TCB | 0 | 0.0035 | 0.0071 | 0.0102 | 0.0135 |
| Tetras | 0 | 0.0048 | 0.0100 | 0.0148 | 0.0200 |
| x-value | 2.00 | 2.11 | 2.23 | 2.35 | 2.45 |
| R-value | — | 12.27 | 12.04 | 12.44 | 11.73 |

EXAMPLE IV

Activated potassium-form zeolite L catalyst was prepared by heating potassium-form zeolite L powder (Toyo Soda) in an oven at 200° C. overnight.

The apparatus of Example III was charged with 47.10 grams of para-dichlorobenzene, 47.13 grams of ortho-dichlorobenzene, 52.54 grams of meta-dichlorobenzene, and 5.00 grams of the activated potassium-form zeolite L catalyst. The charged materials were heated to 96° C. and molecular chlorine was introduced below the surface of the liquid via the hollow bore and outlet orifice at a rate of 0.30 gram per minute for 5.5 hours while the temperature was maintained at 96° C. Samples were taken before the beginning of chlorine introduction and 1, 2, 3, and 5.5 hours after the beginning of chlorine introduction. The samples were analyzed and the x-value and R-value were calculated. The results are shown in Table 4.

TABLE 4

| Time, hours | 0 | 1 | 2 | 3 | 5.5 |
|---|---|---|---|---|---|
| Product Distribution, moles | | | | | |
| Meta-DCB | 0.3660 | 0.3105 | 0.2603 | 0.2120 | 0.1332 |
| Para-DCB | 0.3126 | 0.3209 | 0.3171 | 0.3200 | 0.3124 |
| Ortho-DCB | 0.3213 | 0.2994 | 0.2780 | 0.2594 | 0.2164 |
| 1,2,4-TCB | 0 | 0.0657 | 0.1333 | 0.1915 | 0.3068 |
| 1,2,3-TCB | 0 | 0.0036 | 0.0090 | 0.0101 | 0.0196 |
| 1,2,4,5-Tetra | 0 | Trace | 0.0043 | 0.0072 | 0.0117 |
| 1,2,3,4-Tetra | 0 | 0 | 0 | 0 | Trace |
| x-value | 2.00 | 2.07 | 2.15 | 2.22 | 2.35 |
| R-value | — | 18.25 | 10.02 | 11.07 | 9.80 |

EXAMPLE V

This is a comparative example showing the effect of using a sulfur-promoted ferric chloride catalyst.

The apparatus of Example II was charged with 228.55 grams of ortho-dichlorobenzene of 98.65 percent purity, 0.1179 gram of anhydrous ferric chloride, and 0.0650 gram of elemental sulfur. The charged materials were heated to 110° C. and molecular chlorine was introduced below the surface of the liquid via the dip tube at a rate of 0.46 gram per minute for 4 hours while the temperature was maintained at 110° C. Each hour after the beginning of chlorine introduction, a sample was taken. The sample was then analyzed and the x-value and R-value were calculated. The results are shown in Table 5.

TABLE 5

| Time, hours | 0 | 1 | 2 | 3 | 4 |
|---|---|---|---|---|---|
| Product Distribution, wt. percent | | | | | |
| Meta-DCB | 0.02 | 0 | 0 | 0 | 0 |
| Para-DCB | 1.22 | 1.04 | 0.88 | 0.74 | 0.58 |
| Ortho-DCB | 98.65 | 68.88 | 44.59 | 26.21 | 10.61 |
| 1,4-BCB | 0.03 | 0.01 | 0.01 | 0.01 | 0 |
| 1,2,4-TCB | 0.08 | 18.84 | 34.05 | 44.25 | 49.35 |
| 1,2,3-TCB | 0 | 7.50 | 13.01 | 15.47 | 14.14 |
| 1,2,4,5-Tetra | 0 | 0.26 | 1.33 | 3.09 | 6.86 |
| 1,2,3,4-Tetra | 0 | 0.81 | 3.55 | 8.13 | 16.05 |
| Penta | 0 | 0 | 0 | 0.06 | 0.20 |
| x-value | 2.00 | 2.25 | 2.52 | 2.77 | 3.06 |
| R-value | | 2.24 | 1.99 | 1.77 | 1.47 |

Although the present invention has been described with reference to specific details of certain embodiments thereof, it is not intended that such details should be regarded as limitations upon the scope of invention except insofar as they are included in the accompanying claims.

We claim:

1. A method comprising reacting benzene, chlorobenzene, meta-dichlorobenzene, ortho-dichlorobenzene, or a mixture of two or more thereof with chlorinating agent in a reaction medium comprising a liquid phase and a catalytic amount of zeolite L, zeolite Y, or a mixture thereof, to produce an organic reaction product comprising 1,2,4-trichlorobenzene wherein the x-value of said organic reaction product is in the range of from 2.1 to about 3.2.

2. The method of claim 1 wherein said chlorinating agent is molecular chlorine.

3. The method of claim 1 wherein the reaction temperature is in the range of from about 40° C. to about 200° C.

4. The method of claim 1 wherein the reaction is a semi-batch reaction and the weight ratio of said zeolite L, zeolite Y, or a mixture thereof to said benzene, chlorobenzene, meta-dichlorobenzene, ortho-dichlorobenzene, or a mixture of two or more thereof initially present is in the range of from about 0.1:100 to about 20:100.

5. The method of claim 1 wherein the R-value of said organic reaction product is at least about 2.5.

6. The method of claim 1 wherein the R-value of said organic reaction product is at least about 3.

7. The method of claim 1 wherein the R-value of said organic reaction product is at least about 4.

8. The method of claim 1 wherein the R-value of said organic reaction product is at least about 5.

9. The method of claim 1 wherein the R-value of said organic reaction product is at least about 6.

10. The method of claim 1 wherein the R-value of said organic reaction product is at least about 7.

11. The method of claim 1 wherein the R-value of said organic reaction product is at least about 9.

12. The method of claim 1 wherein the R-value of said organic reaction product is at least about 11.

13. The method of claim 1 wherein the x-value of said organic reaction product is in the range of from about 2.3 to about 3.1.

14. The method of claim 1 wherein the organic feedstock for the reaction comprises at least about 10 percent by weight benzene, chlorobenzene, meta-dichlorobenzene, ortho-dichlorobenzene, or a mixture of two or more thereof.

15. The method of claim 1 wherein said reaction medium comprises a catalytic amount of zeolite Y.

16. The method of claim 1 wherein said reaction medium comprises a catalytic amount of zeolite L.

17. A method comprising reacting meta-dichlorobenzene, ortho-dichlorobenzene, or a mixture thereof with chlorinating agent in a reaction medium comprising a liquid phase and a catalytic amount of zeolite L, zeolite Y, or a mixture thereof, to produce an organic reaction product comprising 1,2,4-trichlorobenzene wherein:
   (a) the feedstock for the reaction comprises at least about 30 percent by weight meta-dichlorobenzene, ortho-dichlorobenzene, or a mixture thereof; and
   (b) the x-value of said organic reaction product is in the range of from about 2.1 to about 3.2.

18. The method of claim 17 wherein said chlorinating agent is molecular chlorine.

19. The method of claim 18 wherein the reaction temperature is in the range of from about 40° C. to about 200° C.

20. The method of claim 18 wherein said reaction medium comprises a catalytic amount of zeolite L.

21. The method of claim 20 wherein the R-value of said organic reaction product is at least about 7.

22. The method of claim 20 wherein the R-value of said organic reaction product is at least about 9.

23. The method of claim 20 wherein the R-value of said organic reaction product is at least about 11.

* * * * *